US012653890B2

(12) United States Patent 　　　(10) Patent No.:　US 12,653,890 B2
Borghi et al.　　　　　　　　　　　(45) Date of Patent:　＊Jun. 16, 2026

(54) INORGANIC NANOPARTICLES COMPOSITIONS IN COMBINATION WITH IONIZING RADIATIONS FOR TREATING CANCER

(71) Applicant: NANOBIOTIX S.A., Paris (FR)

(72) Inventors: Elsa Borghi, Saint-Remy-les-Chevreuse (FR); Laurent Levy, Paris (FR); Agnès Pottier, Paris (FR)

(73) Assignee: NANOBIOTIX S.A., Paris (FR)

( * ) Notice: Subject to any disclaimer, the term of this patent is extended or adjusted under 35 U.S.C. 154(b) by 139 days.

This patent is subject to a terminal disclaimer.

(21) Appl. No.: 18/510,716

(22) Filed: Nov. 16, 2023

(65) Prior Publication Data

US 2024/0100163 A1　　Mar. 28, 2024

Related U.S. Application Data

(63) Continuation of application No. 17/331,674, filed on May 27, 2021, now Pat. No. 11,819,548, which is a (Continued)

(30) Foreign Application Priority Data

Jan. 25, 2013　(EP) ..................................... 13305087

(51) Int. Cl.
$A61K\ 41/00$ 　　　　(2020.01)
$A61K\ 9/14$ 　　　　(2006.01)
(Continued)

(52) U.S. Cl.
CPC ............ $A61K\ 41/0038$ (2013.01); $A61K\ 9/14$ (2013.01); $B82Y\ 5/00$ (2013.01); (Continued)

(58) Field of Classification Search
CPC .......... A61N 5/10–1084; A61N 5/1085–1098; A61N 2005/1085–1098; B82Y 5/00; A61K 41/0038
See application file for complete search history.

(56) References Cited

U.S. PATENT DOCUMENTS 7,367,934 B2　5/2008　Hainfeld et al.
9,700,621 B2　7/2017　Levy et al.
(Continued)

FOREIGN PATENT DOCUMENTS

WO　　WO 2009/147214　　12/2009
WO　　WO 2011/003999　　1/2011
(Continued)

OTHER PUBLICATIONS

Herrera, A., et al., "Breakthrough concept in local treatment for advanced tumors," NTBX Chicago, Jun. 3, 2013, pp. 1-51.
(Continued)

*Primary Examiner* — Thaddeus B Cox
(74) *Attorney, Agent, or Firm* — SALIWANCHIK, LLOYD & EISENSCHENK

(57) ABSTRACT

The present application relates to activable inorganic nanoparticles which can be used in the health sector, in particular in human health, to disturb, alter or destroy target cancerous cells, tissues or organs. It more particularly relates to nanoparticles which can generate a surprisingly efficient therapeutic effect, when concentrated inside the tumor and exposed to ionizing radiations. The invention also relates to pharmaceutical compositions comprising a population of nanoparticles as defined previously, as well as to their uses.

12 Claims, 4 Drawing Sheets
(4 of 4 Drawing Sheet(s) Filed in Color)

Related U.S. Application Data continuation of application No. 16/129,851, filed on Sep. 13, 2018, now Pat. No. 11,020,480, which is a continuation of application No. 14/762,971, filed as application No. PCT/EP2014/051367 on Jan. 24, 2014, now Pat. No. 10,098,952.

(60) Provisional application No. 61/756,533, filed on Jan. 25, 2013.

(51) Int. Cl.
| | | |
|---|---|---|
| *A61N 5/10* | (2006.01) | |
| *B82Y 5/00* | (2011.01) | |

(52) U.S. Cl.
CPC ................. *A61N 2005/1087* (2013.01); *A61N 2005/1089* (2013.01); *A61N 2005/1098* (2013.01)

(56) References Cited

U.S. PATENT DOCUMENTS

| | | | |
|---|---|---|---|
| 9,956,175 | B2 | 5/2018 | Pottier et al. |
| 10,064,962 | B2 | 9/2018 | Pottier et al. |
| 10,098,952 | B2 | 10/2018 | Borghi et al. |
| 10,265,406 | B2 | 4/2019 | Pottier et al. |
| 10,391,058 | B2 | 8/2019 | Germain et al. |
| 10,391,174 | B2 | 8/2019 | Levy et al. |
| 10,413,509 | B2 | 9/2019 | Pottier et al. |
| 10,588,987 | B2 | 3/2020 | Poul et al. |
| 10,765,632 | B2 | 9/2020 | Germain et al. |
| 10,945,965 | B2 | 3/2021 | Pottier et al. |
| 11,020,480 | B2 | 6/2021 | Borghi et al. |
| 11,096,962 | B2 | 8/2021 | Marill et al. |
| 11,191,846 | B2 | 12/2021 | Meyre et al. |
| 11,229,705 | B2 | 1/2022 | Pottier et al. |
| 11,247,054 | B2 | 2/2022 | Levy et al. |
| 11,278,723 | B2 | 3/2022 | Meyre et al. |
| 11,304,902 | B2 | 4/2022 | Pottier et al. |
| 11,357,724 | B2 | 6/2022 | Pottier et al. |
| 11,471,410 | B2 | 10/2022 | Germain et al. |
| 11,471,482 | B2 | 10/2022 | Pottier et al. |
| 11,497,717 | B2 | 11/2022 | Meyre et al. |
| 11,819,548 | B2 | 11/2023 | Borghi et al. |

| | | | |
|---|---|---|---|
| 2002/0061298 | A1 | 5/2002 | Coffey et al. |
| 2002/0177583 | A1 | 11/2002 | Kiss |
| 2008/0171982 | A1 | 7/2008 | Mehier |
| 2010/0040555 | A1 | 2/2010 | Levy et al. |
| 2010/0320402 | A1 | 12/2010 | Wu et al. |
| 2011/0213192 | A1 | 9/2011 | Levy et al. |
| 2012/0203050 | A1 | 8/2012 | Levy et al. |
| 2014/0335015 | A1 | 11/2014 | Pottier et al. |
| 2016/0136304 | A1 | 5/2016 | Poul et al. |
| 2017/0258718 | A1 | 9/2017 | Meyre et al. |
| 2017/0258937 | A1 | 9/2017 | Meyre et al. |
| 2019/0314530 | A1 | 10/2019 | Poul et al. |
| 2021/0353670 | A1 | 11/2021 | Marill et al. |
| 2022/0212008 | A1 | 7/2022 | Meyre et al. |
| 2023/0211175 | A1 | 7/2023 | Borghi et al. |

FOREIGN PATENT DOCUMENTS

| | | |
|---|---|---|
| WO | WO 2011/127061 | 10/2011 |
| WO | WO 2013/087920 | 6/2013 |

OTHER PUBLICATIONS

Maggiorella, L., et al., "Nanoscale radiotherapy with hafnium oxide nanoparticles," *Future Oncology*, Sep. 2012, vol. 8, No. 9, pp. 1167-1181.

Nanobiotix, "Release / Nanobiotix Starts Clinical Trial with Lead Product NBTXR3," Sep. 13, 2011, XP002671267, p. 1, retrieved from internet: URL:http://www. nanobiotix.com/news/release/nanobiotix-starts-clinic-trial-with-lead-product-nbtxr3/, retrieved on Mar. 12, 2012.

Pottier, A., et al., "New Use of Metals as Nanosized Radioenhancers," *Anticancer Research*, Jan. 2014, vol. 34, No. 1, pp. 443-453.

Written Opinion in International Application No. PCT/EP2014/051367, May 20, 2014, pp. 1-8.

Miller, T. R. et al. "Measurement of Tumor Volume By Pet To Evaluate Prognosis in Patients With Advanced Cervical Cancer Treated By Radiation Therapy" *Int. J. Radiation Oncology Biol. Phys.*, 2002, pp. 353-359, vol. 53, No. 2.

Bush, D. A. et al. "Proton-Beam Radiotherapy for Early-Stage Lung Cancer" Chest, Nov. 1999, pp. 1313-1319, vol. 116, No. 5.

Claims as filed in U.S. Appl. No. 18/035,303, filed May 4, 2023, pp. 1-3.

Claims as filed in U.S. Appl. No. 18/039,728, filed Jun. 1, 2023, pp. 1-3.

TUMOR (pink)                                    TUMOR (pink)

2 DAYS AFTER INJECTION          15 DAYS AFTER INJECTION

NANOPARTICLES                          NANOPARTICLES

DISPERSION (blue)                      DISPERSION (blue)

Tumor

NBTXR3

Radiotherapy

INORGANIC NANOPARTICLES COMPOSITIONS IN COMBINATION WITH IONIZING RADIATIONS FOR TREATING CANCER

CROSS-REFERENCE TO RELATED APPLICATIONS

This application is the continuation of U.S. application Ser. No. 17/331,674, filed May 27, 2021, now U.S. Pat. No. 11,819,548, which is the continuation of U.S. application Ser. No. 16/129,851, filed Sep. 13, 2018, now U.S. Pat. No. 11,020,480, which is the continuation of U.S. application Ser. No. 14/762,971, filed Jul. 23, 2015, now U.S. Pat. No. 10,098,952, which is the national stage of International Patent Application No. PCT/EP2014/051367, filed Jan. 24, 2014, which claims the benefit of U.S. Provisional Patent Application No. 61/756,533, filed Jan. 25, 2013.

The present application relates to activable inorganic nanoparticles which can be used in the health sector, in particular in human health, to disturb, alter or destroy target cancerous cells, tissues or organs. It more particularly relates to nanoparticles which can generate a surprisingly efficient therapeutic effect when concentrated inside the tumor and exposed to ionizing radiations. The invention also relates to pharmaceutical compositions comprising a population of nanoparticles as defined previously, as well as to their uses.

BACKGROUND

Cancer is a leading cause of death worldwide, accounting for 7.6 million deaths (around 13% of all deaths) in 2008 (World Health Organization). Cancer is a generic term for a large group of diseases that can affect any part of the body. Other terms used are malignant tumors and neoplasms. Cancer is the uncontrolled growth and spread of abnormal cells. The growths often invade surrounding tissue and can metastasize to distant sites. Metastases are the major cause of death from cancer. Deaths from cancer worldwide are projected to continue rising, with an estimated 13.1 million deaths in 2030.

Cancer treatment requires a careful selection of one or more interventions, such as surgery, radiotherapy and/or chemotherapy. The goal is to cure the disease or considerably prolong life while improving the patient's quality of life.

Radiations of various forms such as X-Rays, gamma-Rays, UV-Rays, laser light, microwaves, and electron beams as well as particle beams of, for example neutrons, carbon ions and protons, have been used to treat malignant diseases. Some of said radiations have been used in such applications, in combination with radiosensitizers. Electromagnetic and ionizing radiations are indeed capable to break the DNA molecule of the cell, thereby preventing said cell from growing and dividing. This effect can be explained by the action of particles or wave which will create ionization that releases electrons and free radicals travelling within a defined volume and generating energy deposit into this volume.

U.S. Pat. No. 7,367,934 B2 relates to a method for enhancing the effects of radiations directed to a tissue or a population of cells in an animal. This method comprises a step of administering an amount of metal nanoparticles to said animal to achieve a concentration in said tissue or said population of cells of the animal of at least about 0.1% metal by weight; and then a step of irradiating the animal with radiation directed to said tissue or said population of cells, wherein said radiation is in the form of X-rays of about 1 keV to about 25,000 keV.

WO 2011/127061 A1 relates to a method for enhancing the effect of radiation directed to a tissue or a population of cells comprising the steps of: (1) administering to an animal an amount of high-Z particles, the high-Z particles comprising a targeting molecule with an affinity for a targeted tissue or a targeted population of cells and a high-Z element; and (2) subsequently irradiating the targeted tissue or targeted population of cells with ionizing radiations; wherein the high-Z particles are administered to the animal in an amount sufficient to achieve a concentration in the targeted tissue or targeted population of cells of less than 0.05% metal by weight.

Inventors herein provide a new and powerful strategy to use their nanoparticles (herein below described) which are able to achieve a very efficient alteration or destruction of target cancerous cells in combination with ionizing radiations, when said nanoparticles are adequately selected and concentrated inside the targeted cancer site, as herein demonstrated.

SUMMARY OF THE INVENTION

Inventors now provide an advantageous composition comprising inorganic particles for use for treating cancer, in particular a composition allowing the destruction of more than about 30%, preferably more than about 44% or more than about 47%, even more preferably more than about 70%, of cancer cells in a tumor volume of a subject (histological response assessment) or inducing at least more than 20% of tumor size reduction (anatomical response assessment) in a subject or inducing at least more than 20% of tumor $^{18}$F-FDG SUV (Standardized Uptake Value) decline (metabolic response assessment) in a subject, when the tumor of said subject is exposed to ionizing radiations.

Once administered, the volume (Vc) of the composition of the invention occupies between 2 and 50% of the tumor volume (Vt). Each inorganic nanoparticle of the composition has a volume (Vin) having an electron density at least 5 times the electron density of the corresponding volume 1 (Vw1) of water.

In a particular embodiment, a method for inducing in a subject suffering from a cancer (i) the destruction of more than 30% of cancer cells in a tumor volume or (ii) at least more than 20% of tumor size reduction is herein described. This method comprises:

administering to a subject suffering from a cancer a composition comprising inorganic nanoparticles, each of said inorganic nanoparticles having a volume (Vin) having an electron density at least 5 times the electron density of the corresponding volume 1 (Vw1) of water, and exposing the tumor (targeted tissue or targeted population of cells) of the subject to ionizing radiations, thereby inducing (i) the destruction of more than 30% of cancer cells in a tumor volume or (ii) at least more than 20% of tumor size reduction when the volume (Vc) of said composition occupies between 2 and 50% of the tumor volume (Vt).

The present document further describes the use of inorganic nanoparticles to prepare a composition for inducing, in a subject suffering from a cancer (i) the destruction (pathological response) of more than about 30%, preferably more than about 44% or 47%, even more preferably more than about 70%, of cancer cells in a tumor volume or (ii) at least more than 20% of tumor size reduction (tumor shrinkage), when the volume (Vc) of said composition occupies between 2 and 50% of the tumor volume (Vt) and when the tumor is exposed to ionizing radiations, wherein each inorganic nanoparticle has a volume (Vin) having an electron density at least 5 times the electron density of the corresponding volume 1 (Vw1) of water.

In a preferred embodiment, said volume composition (Vc) has an electron density of at least 3% of the electron density of the corresponding volume 2 (Vw2) of water, and even more preferably said inorganic nanoparticles provide more than $3 \times 10^{22}$ electrons, preferably more than $7 \times 10^{22}$ electrons, to the tumor mass.

In a further preferred embodiment, these inorganic nanoparticles provide more than $3 \times 10^{22}$ electrons, preferably more than $7 \times 10^{22}$ electrons, to the tumor mass. In another preferred embodiment, the volume composition (Vc) (advantageously further) has an electron density of at least 3% of the electron density of the corresponding volume 2 (Vw2) of water (FIG. 1).

Results presented for the first time in the context of the present invention now demonstrate that a composition comprising high electron density inorganic nanoparticles occupying between 2 and 50% of the tumor volume is able to induce at least more than about 30%, preferably more than about 44% or 47%, even more preferably more than about 70% of cancer cell killing when the inorganic nanoparticles provide at least, preferably more than, $3 \times 10^{22}$ electrons, for example more than about $3.2 \times 10^{22}$ electrons, preferably more than $7 \times 10^{22}$ electrons, to the tumor mass. Each nanoparticle of the composition advantageously has an electron density at least 5 times the electron density of the same nanoparticle composed of water molecules.

DETAILED DESCRIPTION OF THE INVENTION

Inorganic Nanoparticle
Size

In the spirit of the invention, the term "nanoparticle" refers to a product, in particular a synthetic product, with a size in the nanometer range, typically between 1 nm and 500 nm.

The term "crystallite" herein refers to a crystalline product. The size of the crystallite and its structure and composition may be analyzed from X-ray diffractogram.

The term "aggregate of crystallites" refers to an assemblage of crystallites strongly, typically covalently, bound to each other.

The nanoparticle of the invention is typically a crystallite and/or an aggregate of crystallites.

The terms "size of the nanoparticle" and "largest size of the nanoparticle" herein refer to the "largest dimension of the nanoparticle" or "diameter of the nanoparticle". Transmission Electron Microscopy (TEM) can be used to measure the size of the nanoparticle. As well, Dynamic Light Scattering (DLS) can be used to measure the hydrodynamic diameter of nanoparticles in solution. These two methods may further be used one after the other to compare size measurements and confirm said size. A preferred method is DLS (Ref International Standard ISO22412 Particle Size Analysis—Dynamic Light Scattering, International Organisation for Standardisation (ISO) 2008).

The largest dimension of a nanoparticle as herein defined is typically between about 5 nm and about 250 nm, preferably between about 10 nm and about 100 nm or about 200 nm, even more preferably between about 20 nm and about 150 nm.
Shape As the shape of the particle can influence its "biocompatibility", particle having a quite homogeneous shape is preferred. For pharmacokinetic reasons, nanoparticles being essentially spherical, round or ovoid in shape are thus preferred. Such a shape also favors the nanoparticle interaction with or uptake by cells. Spherical or round shape is particularly preferred.

Typically, the largest dimension is the diameter of a nanoparticle of round or spherical shape, or the longest length of a nanoparticle of ovoid or oval shape.
Composition/Structure The inorganic material of the nanoparticle present in the composition preferably has a theoretical (bulk) density of at least 7 and may be selected from any material exhibiting this property and identified in the table from Physical Constants of Inorganic Compounds appearing on pages 4-43 in *Handbook of Chemistry and Physics* (David R. Lide, Editor-In-Chief, 88th Edition, 2007-2008).

The inorganic material constituting the nanoparticle is preferably a material having an effective atomic number $(Z_{eff})$ of at least 25, preferably at least 40 or 41, more preferably at least 50 or 51, more preferably at least 60, 61, 62 or even 63.

Effective atomic number is a term that is similar to atomic number but is used for compounds (e.g. water) and mixtures of different materials (such as tissue and bone) rather than for atoms. Effective atomic number calculates the average atomic number for a compound or mixture of materials. It is abbreviated $Z_{eff}$.

The effective atomic number is calculated by taking the fractional proportion of each atom in the compound and multiplying that by the atomic number of the atom. The formula for the effective atomic number, $Z_{eff}$, is as follows:

$$Z_{eff} = \sqrt[2.94]{f_1 \times (Z_1)^{2.94} + f_2 \times (Z_2)^{2.94} + f_3 \times (Z_3)^{2.94} + \ldots}$$

where
$f_n$ is the fraction of the total number of electrons associated with each element, and
$Z_n$ is the atomic number of each element.

The atomic number (also known as the proton number) is the number of protons found in the nucleus of an atom. It is traditionally represented by the symbol Z. The atomic number uniquely identifies a chemical element. In an atom of neutral charge, atomic number is equal to the number of electrons.

An example is that of water ($H_2O$) which is made up of two hydrogen atoms (Z=1) and one oxygen atom (Z=8). The total number of electrons is 1+1+8=10. The fraction of electrons corresponding to the two hydrogens is 2/10 and the fraction of electrons corresponding to the unique oxygen is (8/10). $Z_{eff}$ of water is therefore:

$$Z_{eff} = \sqrt[2.94]{0.2 \times 1^{2.94} + 0.8 \times 8^{2.94}} = 7.42$$

$Z_{eff}$ participates in the incoming radiation's absorption capacity of nanoparticles.

The inorganic material constituting the nanoparticle is typically selected from an oxide, a metal, a sulfide and any mixture thereof.

When the inorganic material constituting the nanoparticle is an oxide, this oxide is advantageously selected from Cerium (IV) oxide ($CeO_2$), Neodymium (III) oxide ($Nd_2O_3$), Samarium (III) oxide ($Sm_2O_3$), Europium (III) oxide ($Eu_2O_3$), Gadolinium (III) oxide ($Gd_2O_3$), Terbium (III) oxide ($Tb_2O_3$), Dysprosium (III) oxide ($Dy_2O_3$), Holmium oxide ($HO_2O_3$), Erbium oxide ($Er_2O_3$), Thulium (III) oxide ($Tm_2O_3$), Ytterbium oxide ($Yb_2O_3$), Lutetium oxide ($Lu_2O_3$), Hafnium (IV) oxide ($HfO_2$), Tantalum (V) oxide ($Ta_2O_5$), Rhenium (IV) oxide ($ReO_2$), and Bismuth (III) ($Bi_2O_3$). In the context of the present invention, a mixture of inorganic oxides can also be used to prepare the nanoparticle of the invention.

When the inorganic material constituting the nanoparticle is a metal, this metal is advantageously selected from gold (Au), silver (Ag), platinum (Pt), palladium (Pd), tin (Sn), tantalum (Ta), ytterbium (Yb), zirconium (Zr), hafnium (Hf), terbium (Tb), thulium (Tm), cerium (Ce), dysprosium (Dy), erbium (Er), europium (Eu), holmium (Ho), iron (Fe), lanthanum (La), neodymium (Nd), praseodymium (Pr), lutetium (Lu) and mixtures thereof. In the context of the present invention, mixture of metals is also possible. In the context of the present invention, a mixture of an inorganic oxide and of a metal can also be used to prepare the nanoparticle of the invention.

When the inorganic material constituting the nanoparticle is a sulfide, this sulfide is preferably silver sulfide ($Ag_2S$).

Electron Density

The electron density of the material constituting the nanoparticle (crystallites or aggregates of crystallites) is the number of electrons per volume of material expressed in electrons/$cm^3$ ($e^-/cm^3$).

The electron density is calculated using the following equation:

$$\rho_{e\text{-}material}=d_{material}\times e^-_{material}$$

wherein:
i. $\rho_{e\text{-}material}$ corresponds to the electron density of the material constituting the nanoparticle, expressed as the number of electrons per $cm^3$ ($e^-/cm^3$);
ii. $d_{material}$ corresponds to the theoretical (bulk) density of the material constituting the nanoparticle (see table from Physical Constants of Inorganic Compounds, pages 4-43, in *Handbook of Chemistry and Physics*, David R. Lide, Editor-In-Chief, 88th Edition, 2007-2008) and is expressed in g/$cm^3$; and
iii. $e^-_{material}$ corresponds to the number of electrons per gram of material constituting the nanoparticle (see for example Table 5.1, page 63, in *The Physics of Radiation Therapy*, Fourth Edition, Faiz M. Khan, 2010) and is expressed in electrons/g ($e^-/g$).

When the inorganic material constituting the nanoparticle is a metal, the number of electrons per gram of any metallic element may be calculated using the following formula:

$$N_0=N\times Z/A$$

$N_0$=number of electrons per gram of the element
N=Avogadro's number
Z=atomic number of the element
A=atomic weight of the element.
For example:
for gold element, the number of electrons per gram is
$N_0=6.022\times10^{23}\times79/196.96=2.41\times10^{23}$ for lead element, the number of electrons per gram is
$N_0=6.022\times10^{23}\times82/207.2=2.38\times10^{23}$
for iron element, the number of electrons per gram is
$N_0=6.022\times10^{23}\times26/55.845=2.80\times10^{23}$.

For example, for a spherical gold nanoparticle (GNP) with a diameter equal to 100 nm, the electron density of the nanoparticles is 13.9 times the electron density of the corresponding volume of water (i.e. a sphere of diameter equal to 100 nm filled with water molecules).

$$\frac{\rho_{e\text{-}GNP}}{\rho_{e\text{-}water}}=\frac{d_{GNP}\times e^-_{GNP}}{d_{water}\times e^-_{water}}=\frac{19.3\times2.41\times10^{23}}{1.0\times3.34\times10^{23}}=13.9$$

For example, for a spherical iron nanoparticle with a diameter equal to 100 nm, the electron density of the nanoparticles is 6.6 times the electron density of the corresponding volume of water (i.e. a sphere of diameter equal to 100 nm filled with water molecules).

$$\frac{\rho_{e\text{-}ironNP}}{\rho_{e\text{-}water}}=\frac{d_{ironNP}\times e^-_{ironNP}}{d_{water}\times e^-_{water}}=\frac{7.87\times2.80\times10^{23}}{1.0\times3.34\times10^{23}}=6.6$$

When the inorganic material constituting the nanoparticle is typically an oxide or a sulfide, the number of electrons per gram of any material constituting the nanoparticle may be calculated using the following formula:

$$e^-_{material}=N\times(\Sigma Z_{element})/M$$

$e^-_{material}$=number of electrons per gram of the material constituting the nanoparticle
N=Avogadro's number
$Z_{element}$=atomic number of each element constituting the material
M=Molecular weight of the material constituting the nanoparticle.
For example:
For water molecules, the number of electrons per gram is $e^-_{water}=6.022\times10^{23}\times(1+1+8)/18=3.34\times10^{23}$.
For hafnium oxide material, the number of electrons per gram is $e^-_{HfO2}=6.022\times10^{23}\times(72+8+8)/210.49=2.52\times10^{23}$.
For bismuth oxide material, the number of electrons per gram is $e^-_{Bi2O3}=6.022\times10^{23}\times(83+83+8+8+8)/465.96=2.45\times10^{23}$.
For tantalum oxide material, the number of electrons per gram is $e^-_{Ta2O5}=56.022\times10^{23}\times(73+73+8+8+8+8+8)/441.9=2.53\times10^{23}$.
For cerium oxide material, the number of electrons per gram is $e^-_{CeO2}=6.022\times10^{23}\times(58+8+8)/(172.12)=2.59\times10^{23}$.
For example, for a spherical hafnium oxide nanoparticle ($HfO_2$) with a diameter equal to 100 nm, the electron density of the nanoparticles is 7.3 times the electron density of the corresponding volume of water (i.e. a sphere of diameter equal to 100 nm filled with water molecules).

$$\frac{\rho_{e\text{-}HfO2}}{\rho_{e\text{-}water}}=\frac{d_{HfO2}\times e^-_{HfO2}}{d_{water}\times e^-_{water}}=\frac{9.7\times2.52\times10^{23}}{1.0\times3.34\times10^{23}}=7.3$$

For example, for a spherical bismuth oxide nanoparticle ($Bi_2O_3$) with a diameter equal to 100 nm, the electron density of the nanoparticles is 6.5 times the electron density of the corresponding volume of water (i.e. a sphere of diameter equal to 100 nm filled with water molecules).

$$\frac{\rho_{e-Bi2O3}}{\rho_{e-water}} = \frac{d_{Bi2O3} \times e^{-}_{Bi2O3}}{d_{water} \times e^{-}_{water}} = \frac{8.24 \times 2.53 \times 10^{23}}{1.0 \times 3.34 \times 10^{23}} = 6.5$$

For example, for a spherical tantalum oxide nanoparticle ($Ta_2O_5$) with a diameter equal to 100 nm, the electron density of the nanoparticles is 6.25 times the electron density of the corresponding volume of water (i.e. a sphere of diameter equal to 100 nm filled with water molecules).

$$\frac{\rho_{e-Ta2O5}}{\rho_{e-water}} = \frac{d_{Ta2O5} \times e^{-}_{Ta2O5}}{d_{water} \times e^{-}_{water}} = \frac{8.9 \times 2.45 \times 10^{23}}{1.0 \times 3.34 \times 10^{23}} = 6.25$$

For example, for a spherical cerium oxide nanoparticle ($CeO_2$) with a diameter equal to 100 nm, the electron density of the nanoparticles is 5.6 times the electron density of the corresponding volume of water (i.e. a sphere of diameter equal to 100 nm filled with water molecules).

$$\frac{\rho_{e-TCeO2}}{\rho_{e-water}} = \frac{d_{CeO2} \times e^{-}_{CeO2}}{d_{water} \times e^{-}_{water}} = \frac{7.2 \times 2.39 \times 10^{23}}{1.0 \times 3.34 \times 10^{23}} = 5.6$$

Biocompatible Coating

In a preferred embodiment, the nanoparticle used in the context of the present invention to prepare a composition of interest can be coated with a biocompatible material selected from an agent exhibiting stealth property. Indeed, when the nanoparticles of the present invention are administered to a subject via the intravenous (IV) route, a biocompatible coating with a material selected from an agent exhibiting stealth property is particularly advantageous to optimize the biodistribution of the nanoparticles. Said coating is responsible for the so called "stealth property" of the nanoparticle.

Agent exhibiting stealth properties may be an agent displaying a steric group. Such a group may be selected, for example, from polyethylene glycol (PEG); polyethylenoxide; polyvinylalcohol; polyacrylate; polyacrylamide (poly (N-isopropylacrylamide)); polycarbamide; a biopolymer; a polysaccharide such as dextran, xylan and cellulose; collagen; a zwitterionic compound such as polysulfobetain; etc.

In another preferred embodiment, the nanoparticles can be coated with a biocompatible material selected from an agent allowing interaction with a biological target. Such an agent can typically bring a positive or a negative charge on the nanoparticle's surface. This charge can be determined by zeta potential measurements, typically performed on nanoparticle suspensions the concentration of which varies between 0.2 and 10 g/L, the nanoparticles being suspended in an aqueous medium with a pH comprised between 6 and 8.

An agent forming a positive charge on the nanoparticle surface can be for example aminopropyltriethoxisilane or polylysine. An agent forming a negative charge on the nanoparticle surface can be for example a phosphate (for example a polyphosphate, a metaphosphate, a pyrophosphate, etc.), a carboxylate (for example citrate or dicarboxylic acid, in particular succinic acid) or a sulphate.

A full biocompatible coating of the nanoparticle or aggregate may be advantageous, in particular in the intravenous (IV) context, in order to avoid interaction of the particle surface with any recognition element (macrophage, opsonins, etc.). The "full coating" implies the presence of a very high compactness of biocompatible molecules able to create at least a complete monolayer on the surface of the particle.

The biocompatible coating allows in particular the nanoparticle stability in a fluid, such as a physiological fluid (blood, plasma, serum, etc.), any isotonic media or physiological medium, for example media comprising glucose (5%) and/or NaCl (0.9%), which is required for a pharmaceutical administration.

Stability may be confirmed by dry extract quantification using a drying oven and measured on a nanoparticle suspension prior to and after filtration, typically on a 0.22 or 0.45 µm filter.

Advantageously, the coating preserves the integrity of the particle in vivo, ensures or improves the biocompatibility thereof, and facilitates an optional functionalization thereof (for example with spacer molecules, biocompatible polymers, targeting agents, proteins, etc.).

Targeting

A particular nanoparticle according to the present invention can further comprise a targeting agent allowing its interaction with a recognition element present on the target cell. Such a targeting agent typically acts once the nanoparticles are accumulated on the target site. The targeting agent can be any biological or chemical structure displaying affinity for molecules present in the human or animal body. For instance it can be a peptide, an oligopeptide or polypeptide, a protein, a nucleic acid (DNA, RNA, SiRNA, tRNA, miRNA, etc.), a hormone, a vitamin, an enzyme, the ligand of a molecule expressed by a pathological cell, in particular the ligand of a tumor antigen, hormone receptor, cytokine receptor or growth factor receptor. Said targeting agents can be selected for example from the group consisting of LHRH, EGF, a folate, anti-B-FN antibody, E-selectin/P-selectin, anti-IL-2Rα antibody, GHRH, etc.

Composition

Another particular object herein described relates to a pharmaceutical composition comprising nanoparticles such as defined hereinabove, preferably together with a pharmaceutically acceptable carrier or vehicle.

A typical object of the invention is a composition inducing in a mammal subject having a tumor, preferably in a human subject having a tumor, (i) the destruction of more than 30% of cancer cells in a tumor volume or (ii) at least more than 20% of tumor size reduction when the volume (Vc) of said composition occupies between 2 and 50% of the tumor volume (Vt) and when the tumor is exposed to ionizing radiations, wherein the composition comprises inorganic nanoparticles having a volume (Vin) having an electron density at least 5 times the electron density of the corresponding volume 1 (Vw1) of water.

In a typical embodiment, the volume of the mammal's tumor is between 3 $cm^3$ (3 cc) and 5000 $cm^3$ (5000 cc).

The composition can be in the form of a solid, liquid (particles in suspension), aerosol, gel, paste, and the like. Preferred compositions are in a liquid or a gel form. Particularly preferred compositions are in liquid form.

The carrier which is employed can be any classical support for the skilled person, such as a saline, isotonic, sterile, buffered solution, a non-aqueous vehicle solution and the like.

The composition can also comprise stabilizers, sweeteners, surfactants, polymers and the like.

It can be formulated for example as ampoule, aerosol, bottle, tablet, capsule, by using techniques of pharmaceutical formulation known by the skilled person.

Generally, the composition, in liquid or gel form, comprises between about 0.05 g/L and about 450 g/L of nanoparticles, between about 0.05 g/L and about 150 g/L of nanoparticles, preferably at least about 10 g/L, 20 g/L, 40 g/L, 45 g/L, 50 g/L, 55 g/L, 60 g/L, 80 g/L, 100 g/L, 150 g/L, 200 g/L, 250 g/L, 300 g/L, 350 g/L or 400 g/L of nanoparticles.

The concentration of nanoparticles in the composition can be measured by dry extract. A dry extract is ideally measured following a drying step of the suspension comprising the nanoparticles in a drying oven.

Administration Route

The nanoparticles of the invention can be administered to the subject using different possible routes such as local (intra-tumoral (IT), intra-arterial (IA)), subcutaneous, intra venous (IV), intra-dermic, airways (inhalation), intra peritoneal, intra muscular, intra-articular, intra-thecal, intra-ocular or oral route (per os), preferably using IT, IV or IA.

Repeated injections or administrations of nanoparticles can be performed, when appropriate.

Solid Tumor

The invention can be used to treat any type of malignant solid tumors, in particular of epithelial, neuroectodermal or mesenchymal origin, as well as lymphatic cancers. The nanoparticles can also be used for advanced stage tumors which cannot be surgically removed.

The nanoparticles herein described are in particular intended to be used to treat cancer where radiotherapy is a classical treatment or is the most appropriate treatment for a particular subject, or where radiotherapy could be indicated. Such cancer may be selected in particular from the group consisting of skin cancer, including malignant neoplasms associated with AIDS, melanoma; squamous cancer; central nervous system tumors including brain, cerebellum, pituitary, spinal cord, brain stem, eye and orbit; head and neck tumors; lung cancers; breast cancers; gastrointestinal tumors such as liver and hepatobiliary tract cancers, colon, rectum and anal cancers, stomach, pancreas, oesophagus cancer; male genitourinary tumors such as prostate, testis, penis and urethra cancers; gynecologic tumors such as uterine cervix, endometrium, ovary, fallopian tube, vagina and vulvar cancers; adrenal and retroperitoneal tumors; sarcomas of bone and soft tissue, regardless of the localization; and pediatric tumors such as Wilm's tumor, neuroblastoma, central nervous system tumors, Ewing's sarcoma, etc.

Tumor Volume (Vt) Evaluation Before Treatment

Tumor volume imaging includes radiography, computed tomography (CT), magnetic resonance imaging (MRI), ultrasound (US), single photon emission tomography (SPECT), and positron emission tomography (PET) as known by the skilled person. All those techniques are used to evaluate the tumor volume. CT and MRI are the most commonly used procedures for treatment planning.

MRI uses radio frequency power in the presence of a strong magnetic field to perturb protons, either in water or in fatty acid chains, and to allow them producing a radio frequency signal in return. This signal can be registered with the use of receiver coils. Gradients can be applied during the application of the radio frequency pulse or during the reception of this signal to spatially encode it and create a map of the signal in the body. Tissue characteristics such as T1, T2, magnetic susceptibility, and resonant frequencies produced by fat, water, and other compounds can be detected in the image.

Computed tomography (CT) imaging is based on the variable absorption of X-rays by different tissues, and provides a cross-sectional imaging. The origin of the word "tomography" is from the Greek words "tomos" meaning "slice" or "section" and "graphe" meaning "drawing". A CT imaging system produces cross-sectional images of the bones and soft tissues inside the body. CT images can be combined to create 3D images.

Evaluation of the Volume of Composition (Vc) within the Tumor Volume

The nanoparticles of the present invention are composed of high electron density material. They are intrinsically radio-opaque (i.e. they absorb X-rays) and can be easily visualized when using typically radiography and computed tomography.

The volume of composition (Vc) within the tumor volume (Vt) can be calculated using the computed tomography (CT) imaging technique. The nanoparticles used to prepare the composition will create a marked contrast in the CT images due to the difference of electron density between the tumor tissue and the nanoparticles.

The Hounsfield number is a normalized value of the calculated X-ray absorption coefficient of a pixel (picture element) in a computed tomogram, expressed in Hounsfield units (HU), where the CT number of air is −1000 (HU=−1000) and that of water is zero (HU=0). For inorganic nanoparticles with high electron density, separation between tissues and nanoparticles occurs typically around HU values of 120 or 150. Above HU values of typically 120 or 150 up to 200, no more soft tissues densities can be found.

Thus the volume of composition (Vc)—the volume occupied by the nanoparticles (HU typically above 120 or 150)—can be calculated.

FIG. 2 shows typical CT images of a tumor with presence of high density nanoparticles (composed of hafnium oxide material). In this figure, an aqueous suspension of nanoparticles (composed of hafnium oxide material) was injected directly into the tumor (intra-tumoral administration). $N_0$ leak of nanoparticles from the tumor mass (<10%) following injection thereof as well as persistence of said nanoparticles within the tumor structure have both been demonstrated (L. Maggiorella et al. Nanoscale radiotherapy with hafnium oxide nanoparticles. Future Oncology, 2012, 8(9); 1167-1181).

Typically, the volume of composition (Vc) occupies between 2% and 55% of the tumor volume. More preferably, the volume of composition occupies between 2% and 50%, 2% and 45%, 2% and 40%, 2% and 35%, 2% and 30%, 2% and 25%, and even more preferably between 2%, 2.5, 3 or 5% and 20%, 15% or 10% of the tumor volume.

Calculation of the Electron Density in the Volume Occupied by the Nanoparticles, i.e. The Volume of Composition (Vc) within the Tumor Volume The electron density of the volume of composition (Vc) is calculated using a calibration curve established using a CT scanner.

In a first step, the volume of composition (Vc)—the volume occupied by the nanoparticles (HU above typically 120 or 150 or 200)—is calculated.

In a second step, within the calculated volume (Vc), an histogram corresponding to the distribution of HU values above typically 120 or 150 or 200, is established. The histogram represents the occurrences of voxels related to specific HU values above a specific threshold, typically 120 HU or 150 HU or 200 HU. The mean HU value for the distribution of nanoparticles is obtained using the following equation:

Mean $HU=\Sigma(HU \times occurrence)/\Sigma occurrences$.

A calibration curve is used where the Hounsfield number (HU) is plotted against an increased concentration of the nanoparticles either in a suspension or in a gel. A typical example of calibration curve is presented for gold nanoparticles with size ranging from 15 nm up to 105 nm (GNPs) in FIG. 3.

From the calibration curve, a mean concentration of nanoparticles is calculated ($X_{mean}$ in g/L).

In a third step, the volume of nanoparticles ($V_{NP}=\Sigma Vin$) within Vc is calculated as follows:

$$V_{NP} \text{ (cm}^3) = X_{mean} \times Vc \text{ (cm}^3)/d_{material} \text{ (g/cm}^3)/1000 \text{ (cm}^3)$$

The following equation is then used to calculate the electron density (number of electrons per volume) of the volume of composition:

$$\rho_{e-C}[(Vc-V_{NP})\rho_{e-eau}+V_{NP} \times \rho_{e-material}]/Vc$$

Where, $\rho_{e-C}$=electron density of the volume of composition (number of electrons per cm$^3$);

$\rho_{e-eau}$=electron density of water;

$\rho_{e-material}$=electron density of the material constituting the nanoparticles.

Due to the absence of nanoparticle leakage from the tumor mass following local injection of nanoparticle suspension, the volume of composition corresponds to the volume of the nanoparticle suspension which has been injected into the tumor, and the mean concentration of nanoparticles in the volume of composition corresponds to the concentration of the nanoparticle suspension which has been injected into the tumor.

Calculation of the Quantity of Electrons Provided by the Nanoparticles to the Tumor Volume The quantity of electrons provided by the nanoparticles is calculated using the following equation:

$$\text{Quantity of electrons} = V_{NP} \text{ (cm3)} \times \rho_{e-material}$$

Radiotherapy Sources

The nanoparticles of the invention can be used in many fields, particularly in human or veterinary medicine. Nanoparticles and compositions according to the invention, as herein described, are preferably for use in an animal, preferably in a mammal (for example in the context of veterinary medicine), even more preferably in a human being, as a therapeutic agent, in particular in oncology, preferably when the nanoparticle is exposed to ionizing radiations. Ionizing radiations includes typically X-Rays, gamma-Rays, UV-Rays, electron beams as well as particle beams of, for example, neutrons, carbon ions and protons.

In a particular embodiment, the present invention relates to a method of inducing in a subject suffering from a cancer (i) the destruction of more than about 30%, for example more than about 35%, 40%, 44% or 45%, preferably more than about 47%, for example more than about 50%, 55%, 60%, 65% and 68%, even more preferably more than about 70% of cancer cells in a tumor volume, or (ii) at least 15%, 20%, preferably more than 20% of tumor size reduction, comprising:

administering to a subject a composition having a volume (Vc) occupying between 2 and 50% of the tumor volume (Vt), said composition comprising inorganic nanoparticles, each inorganic nanoparticle having a volume (Vin) having an electron density at least 5 times the electron density of the corresponding volume 1 (Vw1) of water; and exposing the tumor of the subject to ionizing radiations.

In a preferred embodiment, the volume composition (Vc) has an electron density of at least 3% of the electron density of the corresponding volume 2 (Vw2) of water. Even more preferably, the inorganic nanoparticles provide at least, preferably more than $3 \times 10^{22}$ electrons, for example more than about $3.2 \times 10^{22}$ electrons, preferably more than $7 \times 10^{22}$, electrons to the tumor mass.

Under the effect of ionizing radiations, in particular X-Rays, gamma-rays, radioactive isotopes and/or electron beams, the nanoparticles are activated, or in other terms excited, and produce electrons and/or high energy photons. Those electrons and/or high energy photons emitted after ionization will be involved in the direct and/or indirect cell damage, possibly via free radicals generation, and ultimately for cells destruction, resulting in a better outcome for the patient. Surprisingly, inventors discovered that the high electron density of each nanoparticle together with the quantity of electrons provided by the nanoparticles to the tumor mass, are responsible for a markedly increased efficiency of the radiotherapy.

The particles can be excited within a large range of total dose of radiations.

Amounts and schedules (planning and delivery of irradiations whichever fraction dose, fraction delivery schema, total dose alone or in combination with other anticancer agents, etc.) are defined for any disease/anatomical site/disease stage/patient/setting/patient age (children, adult, elderly patient), and constitute the standard of care for any specific situation.

The irradiation can be applied at any time after administration of the nanoparticles, on one or more occasions, by using any currently available system of radiotherapy or radiography.

As indicated previously, appropriate radiations or sources of excitation are preferably ionizing radiations and can advantageously be selected from the group consisting of X-Rays, gamma-Rays, electron beams, ion beams and radioactive isotopes or radioisotopes emissions.

X-Rays is a particularly preferred source of excitation.

Ionizing radiations are typically of about 2 KeV to about 25 000 KeV, in particular of about 2 KeV to about 6000 KeV (i.e. 6 MeV) (LINAC source), or of about 2 KeV to about 1500 KeV (such as a cobalt 60 source).

In general and in a non-restrictive manner, the following X-Rays can be applied in different cases to excite the particles:

Superficial X-Rays of 2 to 50 keV: to excite nanoparticles near the surface (penetration of a few millimeters);

X-Rays of 50 to 150 keV: in diagnostic but also in therapy;

X-Rays (ortho voltage) of 200 to 500 keV which can penetrate a tissue thickness of 6 cm;

X-Rays (mega voltage) of 1000 keV to 25,000 keV.

Radioactive isotopes can alternatively be used as an ionizing radiation source (named as curietherapy or brachytherapy). In particular, Iodine I$^{125}$ (t½=60.1 days), Palladium Pd$^{103}$ (t½=17 days), Cesium Cs$^{137}$, Strontium $^{89}$Sr (t½=50.5 days), Samarium $^{153}$Sm (t½=46.3 hours), and Iridium Ir$^{192}$, can advantageously be used.

Charged particles such as proton beams, ions beams such as carbon, in particular high-energy ion beams, can also be used as an ionizing radiation source and/or neutron beams.

Electron beams may also be used as an ionizing radiation source with energy comprised between 4 MeV and 25 MeV.

Specific monochromatic irradiation sources could be used for selectively generating X-rays radiation at energy close to or corresponding to the desired X-ray absorption edge of the atoms constituting the metallic material.

Preferentially sources of ionizing radiations may be selected from Linear Accelerator (LINAC), Cobalt 60 and brachytherapy sources.

Assessment of Objective Tumor Response

Tumor Size Evaluation (Anatomical Response Criteria)

Assessment of the change in tumor burden is an important feature of the clinical evaluation of cancer therapeutics: both tumor shrinkage (objective response) and disease progression are useful endpoints in clinical trials.

The use of tumor regression (tumor size reduction) as a meaningful endpoint for screening new agents for evidence of anti-tumor effect is supported by years of evidence suggesting that, for many solid tumors, agents which produce tumor shrinkage in a proportion of patients have a reasonable chance (albeit imperfect) of subsequently demonstrating an improvement in overall survival or quality of life, both gold standards for measuring clinical benefit.

In 1981, the World Health Organization (WHO) first published tumor response criteria. New criteria, known as RECIST (Response Evaluation Criteria in Solid Tumors), were published in 2000 and 2009. In the above mentioned tumor response criteria, imaging techniques such as CT, MRI, or other technologies are used for the evaluation of the tumor size.

Percentage (%) of Cancer Cell Killing Evaluation

Histological examination is used to detect residual cancer cells typically after preoperative therapy. Currently, the pathological response evaluation of the primary lesion can be performed using definitions employed in clinical trials such as, but not exhaustively, the Japanese pathological response criteria, the Abersen classification, the GEPARDO classification, and the NSABP B18 classification.

Molecular Imaging (Metabolic Response Criteria)

Among several pursued molecular imaging approaches for treatment monitoring, such as dynamic contrast-enhanced MRI, diffusion-weighted MRI, MR spectroscopy, optical imaging and contrast-enhanced ultrasound, PET with the glucose analog $^{18}$F-FGD ((18)fluorodeoxyglucose positron emission tomography) is clinically the most used.

Lesser or no decline in $^{18}$F-FGD uptake by the tumor was seen as a sign of the absence of tumor response. Those tumors with a continuing decline in $^{18}$F-FGD uptake over time were the most likely to have complete pathological responses by histology at the end of therapy. Tumor $^{18}$F-FGD uptake also declined more rapidly than did tumor size with effective treatment.

Two basic approaches can be considered for assessing the metabolic changes of treatment: qualitative and quantitative. For quantitative analysis, the SUV (Standardized Uptake Value) is the widely used metric for assessing tissue accumulation of tracers. SUV can be normalized to body mass, lean body mass (SUL) or body surface area. Typically, the percentage decline in tumor SUV may be used as a method of quantification for assessing objective tumor response to therapy. However, absolute SUV determinations may also be used.

Molecular Markers for Monitoring Tumor Response to Treatment

The measure of markers specifically secreted by cancer cells into the blood may be used to monitor tumor response to therapy. In some malignant tumors, including prostate, ovarian, and thyroid cancers, tumor markers (prostate-specific antigen, CA125, and thyroglobulin) are used to monitor tumor response to treatment.

Classical cancer management systematically implies the concurrence of multimodality treatments (combination of radiotherapy and chemotherapy for example).

The herein described nanoparticles submitted to radiations, in particular in the context of radiotherapy, can be used in association with every different cancer therapy protocol. Such a protocol can be selected from the group consisting of surgery, radiosurgery, chemotherapy, a treatment comprising administration of cytostatic(s), cytotoxic(s), a targeted therapy, an immunotherapy, radionuclides, in particular immunoradionuclides, and any other biological or inorganic product intended to treat cancer.

Other aspects and advantages of the invention will become apparent in the following examples, which are given for purposes of illustration and not by way of limitation.

BRIEF DESCRIPTION OF THE FIGURES

The patent or application file contains at least one drawing executed in color. Copies of this patent or patent application publication, with color drawing(s), will be provided by the Office upon request and payment of the necessary fee.

HU value as a function of [Au] (g/L) of GOLD-15: diamond dots.

HU value as a function of [Au] (g/L) of GOLD-30: square dots.

HU value as a function of [Au] (g/L) of GOLD-60: triangle dots.

HU value as a function of [Au] (g/L) of GOLD-80: cross dots.

HU value as a function of [Au] (g/L) of GOLD-105: + dots.

Figure 1:
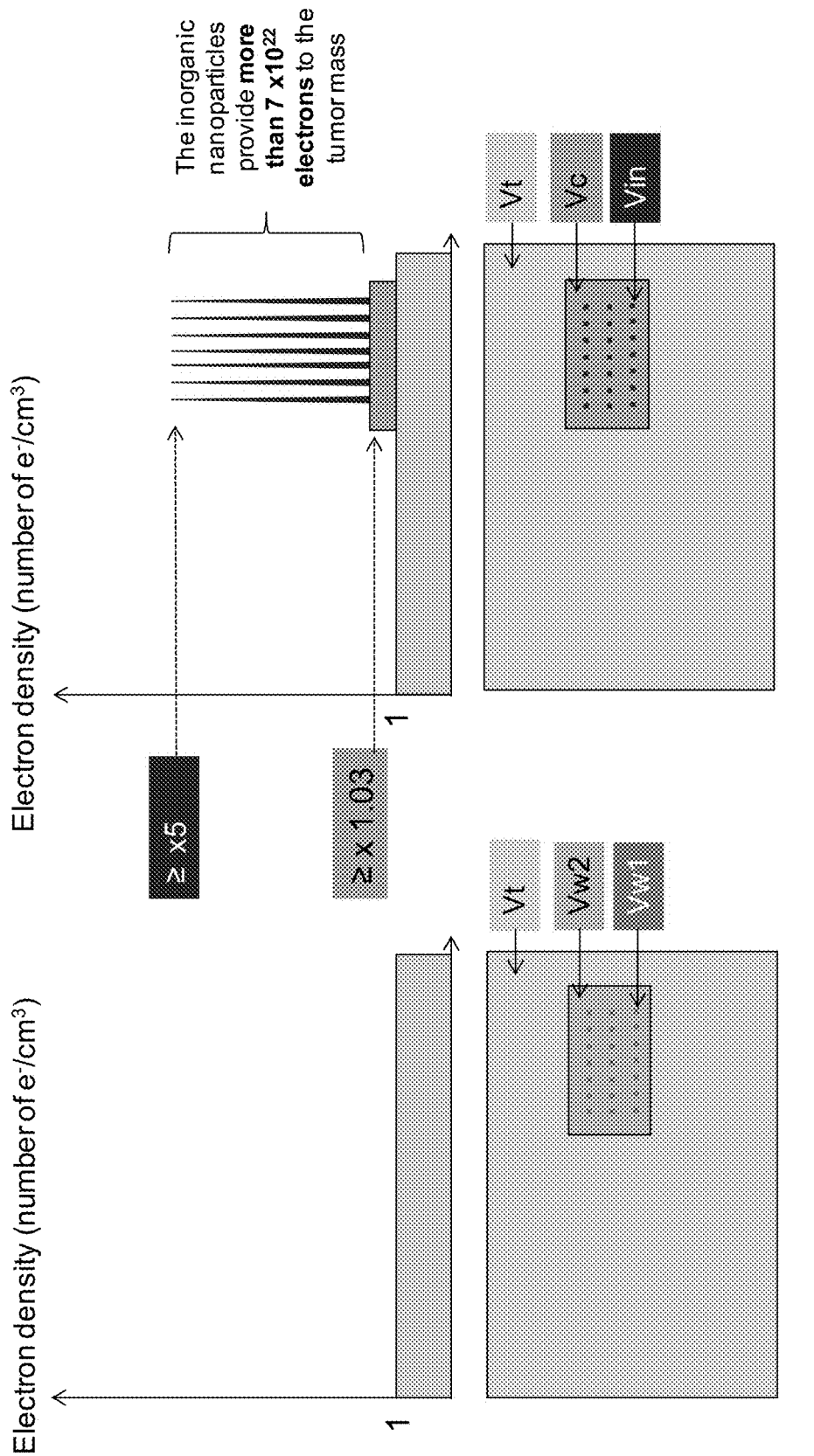
FIG. 1 shows that, once administered, the volume (Vc) of the composition of the invention occupies between 2 and 50% of the tumor volume (Vt). Each inorganic nanoparticle of the composition has a volume (Vin) having an electron density at least 5 times the electron density of the corresponding volume 1 (Vw1) of water. These inorganic nanoparticles provide at least, preferably more than $3 \times 10^{22}$ electrons, for example more than about $3.2 \times 10^{22}$ electrons, preferably more than $7 \times 10^{22}$ electrons, to the tumor mass. The volume composition (Vc) (further) has an electron density of at least 3% of the electron density of the corresponding volume 2 (Vw2) of water.
Figure 2:
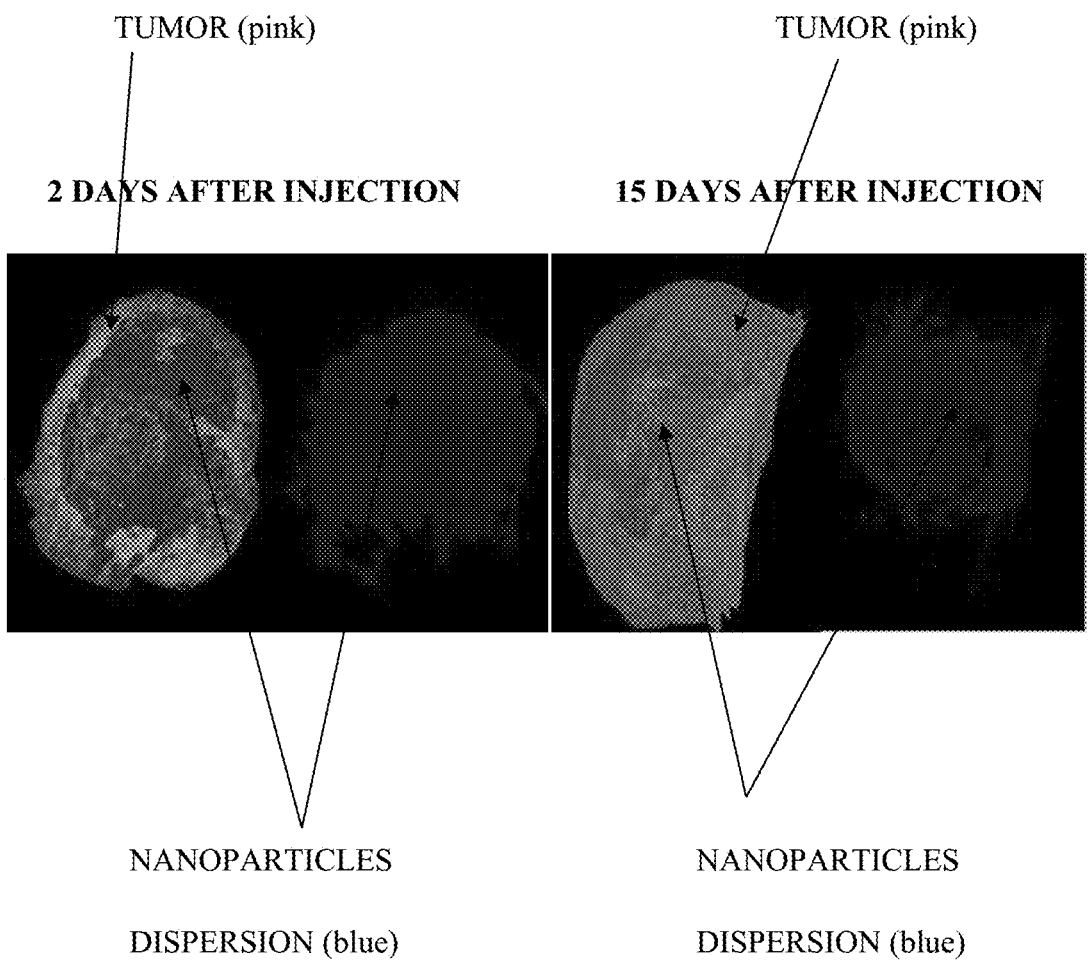
FIG. 2 shows the distribution and dispersion over time of a biocompatible suspension of $HfO_2$ nanoparticles after intra tumoral injection into Swiss nude mice bearing HCT116 tumor. Computed Tomography has been performed on tumor, 2 and 15 days following injection.
Figure 3:
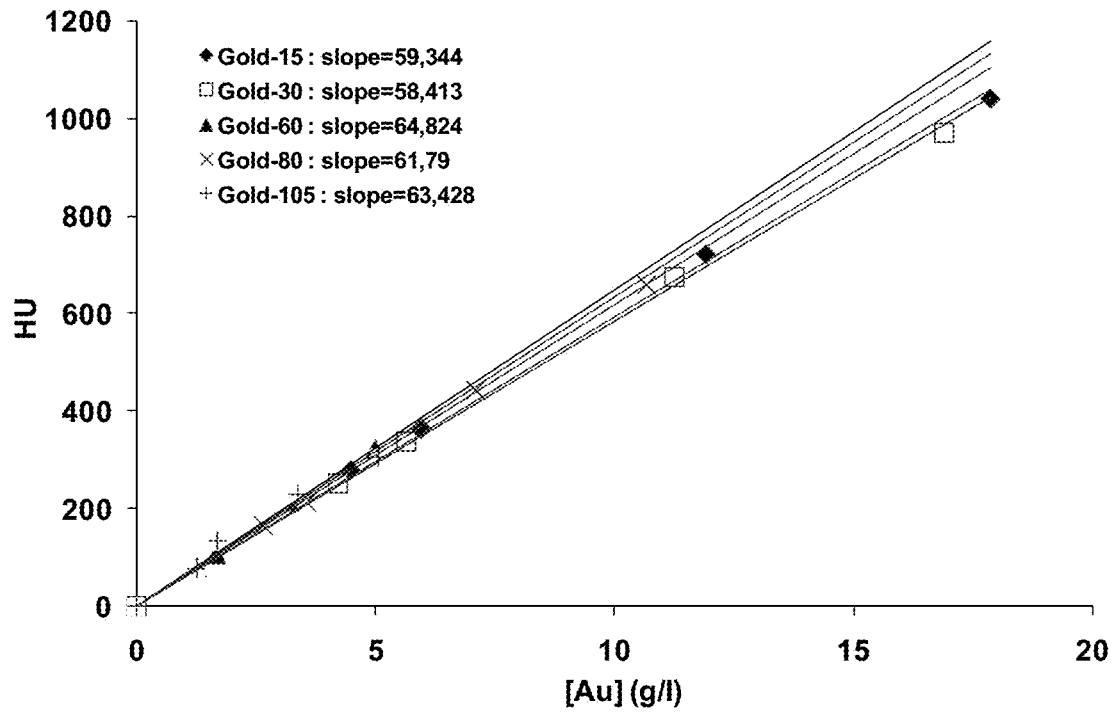
FIG. 3 shows the X-ray attenuation as a function of gold concentration for gold nanoparticles with sizes equal to 15 nm (GOLD-15), 30 nm (GOLD-30), 60 nm (GOLD-60), 80 nm (GOLD-80) and 105 nm (GOLD-105).
Figure 4:
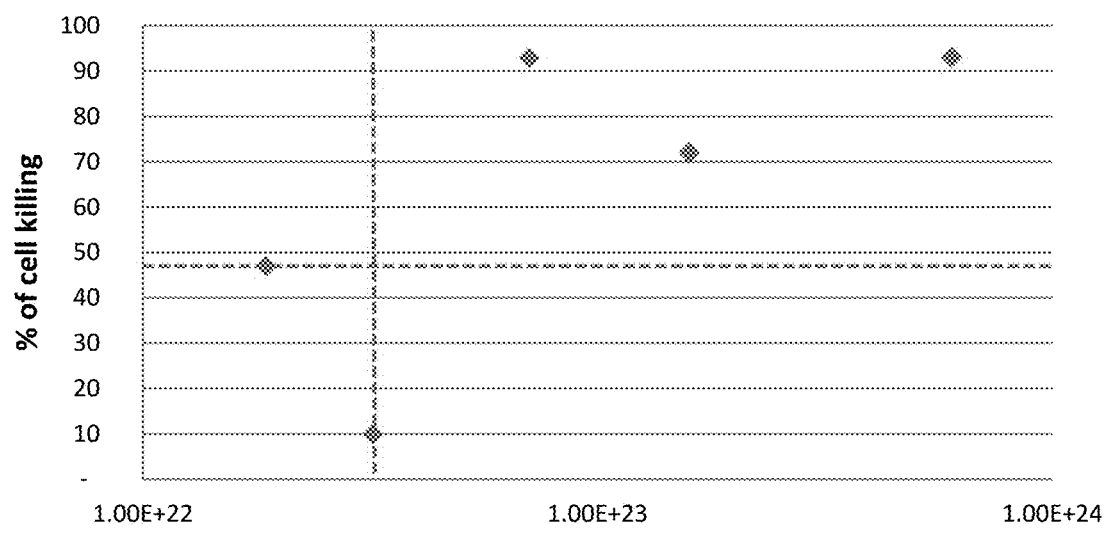

FIG. 4 shows the % of cell killing (postoperative pathological examination) after the treatment at the time of surgery. More than 70% of cell killing was observed for patients having received the high electron density nanoparticle suspension, intra-tumorally injected within the tumor mass such that the quantity of electrons provided by the nanoparticles to the tumor mass is more than $7 \times 10^{22}$.

Figures 5A, 5B:

FIGS. 5A-5B show the distribution and dispersion over time (during all sessions of radiotherapy: 2*25Gy) of a biocompatible suspension of $HfO_2$ nanoparticles after intra tumoral injection into a human subject bearing a soft tissue sarcoma of the extremity. Computed Tomography has been performed on tumor, 1 day (before the first session of radiotherapy; FIG. 5A) and 65 days (after all sessions of radiotherapy, before surgery) following injection (FIG. 5B). The tumor size reduction (tumor volume evolution) is of 53%.

EXAMPLE

A composition comprising hafnium oxide nanoparticles with a concentration equal to 53 g/L is intra-tumorally injected in patients with advanced soft tissue sarcomas of the limbs. The injection volume corresponds to 2.5% of the tumor volume at baseline. Patients received 50Gy of radiation therapy during 5 weeks and then underwent tumor resection.

The following table recapitulates

The tumor volume at baseline (cm³);

The composition volume which is the volume of nanoparticle (composed of hafnium oxide material) suspension which has been intra-tumorally injected and corresponds to 2.5% of the tumor volume at baseline (cm³);

the nanoparticle concentration, equal to 53 g/L;

the electron density of each nanoparticle (with volume Vin) with respect to the electron density of same nanoparticle (with volume Vw1) composed of water molecules:

$$\frac{\rho_{e-HfO2}}{\rho_{e-water}} = \frac{d_{HfO2} \times e_{HfO2}^-}{d_{water} \times e_{water}^-} = \frac{9.6 \times 2.52 \times 10^{23}}{1.0 \times 3.34 \times 10^{23}} = 7.3;$$

the electron density of the volume composition (Vc) with respect to the electron density of the same volume (Vw2) composed of water molecules:

$$\frac{(Vc - V_{HfO2})\rho_{e-eau} + V_{HfO2} \times \rho_{e-HfO2}}{V_c \times \rho_{e-eau}} = 1.034;$$

the quantity of electrons given by the nanoparticles to the tumor mass:

Quantity of electrons=$V_{HfO2}$ (cm3)$\times \rho_{e-HfO2}$ (e−/cm3); and

% of nanoparticles within the tumor, expressed as weight of nanoparticles by weight of tumor (e.g. 0.13% refers to 0.13 g of nanoparticles per 100 g of tumor).

FIG. 4 shows the % of cell killing (postoperative pathological examination) after the treatment at the time of surgery. More than 70% of cell killing was observed for patient having received the high electron density nanoparticle suspension, intra-tumorally injected within the tumor mass such that the quantity of electrons provided by the nanoparticles to the tumor mass is of at least $7 \times 10^{22}$.

Interestingly, the percentage (%) of nanoparticles within the tumor expressed as weight of nanoparticles by weight of tumor is equal to 0.13% (0.13% refers to 0.13 g of nanoparticles per 100 g of tumor). This value corresponds to 0.11% of hafnium element within the tumor (i.e. 0.11 g of Hafnium element per 100 g of tumor). This % of nanoparticles by weight does not enhance markedly the tumor response to radiotherapy unless the quantity of electrons provided by the nanoparticles to the tumor mass is more than $3 \times 10^{22}$, preferably more than $7 \times 10^{22}$.

Results presented here demonstrate that only a composition comprising high electron density inorganic nanoparticles (i.e. each nanoparticle has an electron density at least 5 times the electron density of the same nanoparticle composed of water molecules) occupying between 2 and 50% of the tumor volume are able to induce more than 44% or 47%, preferably more than 70% of cancer cell killing when the inorganic nanoparticles provide more than $3 \times 10^{22}$, preferably more than $7 \times 10^{22}$ electrons to the tumor mass.

We claim:

1. A method for treating solid tumor cancer comprising administering to a human subject suffering from the solid tumor cancer by intra-tumoral injection a composition comprising a suspension of inorganic nanoparticles, determining the tumor volume, determining the volume of the composition comprising the inorganic nanoparticles within the tumor volume by radiography or computed tomography, and exposing the tumor of the human subject to ionizing radiation, wherein the inorganic nanoparticles provide more than $7 \times 10^{22}$ electrons to the tumor, the inorganic material constituting the nanoparticles has a theoretical (bulk) density of at least 7 and an effective atomic number ($Z_{eff}$) of at least 25, and the volume of the composition (Vc) occupies between 2% and 55% of the tumor volume.

2. The method according to claim 1, wherein said ionizing radiation is selected from X-rays, ion beams, electron beams, gamma-rays, or a radioactive isotope.

| | | 55.0 | 55.0 | 95.9 | 158.0 | 212.0 | 476.0 | 1814.4 |
|---|---|---|---|---|---|---|---|---|
| Vt: Tumor volume (cm3) | | 55.0 | 55.0 | 95.9 | 158.0 | 212.0 | 476.0 | 1814.4 |
| Vc: Composition volume (2.5% of the tumor volume) (cm3) | | 1.4 | 1.4 | 2.4 | 4.0 | 5.3 | 11.9 | 45.0 |
| Xmean: Mean concentration (g/L) | | 53.0 | 53.0 | 53.0 | 53.0 | 53.0 | 53.0 | 53.0 |
| Electron density of each nanoparticle with respect to the electron density of same nanoparticle composed of water molecules: e-density (Vin)/e-density (Vw1) | ρ e⁻ Vin/ ρ e⁻ vw1 | 7.3 | 7.3 | 7.3 | 7.3 | 7.3 | 7.3 | 7.3 |
| Electron density of the volume composition (Vc) with respect to electron density of the same volume composed of water molecules: e-density (Vc)/e-density (Vw2) | ρ e⁻ vc/ ρ e⁻ vw2 | 1.03442 3.4% | 1.03442 3.4% | 1.03442 3.4% | 1.03442 3.4% | 1.03442 3.4% | 1.03442 3.4% | 1.03442 3.4% |
| quantity of e-given by the nanoparticles to the tumor mass | | 1.87E+22 | 1.87E+22 | 3.20E+22 | 5.27E+22 | 7.07E+22 | 1.59E+23 | 6.00E+23 |
| % of nanoparticles within the tumor expressed in weight of nanoparticles by weight of tumor | | 0.13% | 0.13% | 0.13% | 0.13% | 0.13% | 0.13% | 0.13% |
| % of cancer cell killing | | 44 | 47 | 10 | 55 | 93 | 72 | 93 |

3. The method according to claim 1, wherein said composition has a volume that is between 2% and 45% of the tumor volume.

4. The method according to claim 1, wherein the inorganic material constituting the nanoparticles is selected from an oxide, a metal, a sulfide and any mixture thereof.

5. The method according to claim 4, wherein the inorganic material constituting the nanoparticles is a metal oxide and is selected from Cerium (IV) oxide ($CeO_2$), Neodymium (III) oxide ($Nd_2O_3$), Samarium (III) oxide ($Sm_2O_3$), Europium (III) oxide ($Eu_2O_3$), Gadolinium (III) oxide ($Gd_2O_3$), Terbium (III) oxide ($Tb_2O_3$), Dysprosium (III) oxide ($Dy_2O_3$), Holmium oxide ($Ho_2O_3$), Erbium oxide ($Er_2O_3$), Thulium (III) oxide ($Tm_2O_3$), Ytterbium oxide ($Yb_2O_3$), Lutetium oxide ($Lu_2O_3$), Hafnium (IV) oxide ($HfO_2$), Tantalum (V) oxide ($Ta_2O_5$), Rhenium (IV) oxide ($ReO_2$), and Bismuth (III) oxide ($Bi_2O_3$) and any mixture thereof.

6. The method according to claim 4, wherein the inorganic material constituting the nanoparticles is a metal selected from gold (Au), silver (Ag), platinum (Pt), palladium (Pd), tin (Sn), tantalum (Ta), ytterbium (Yb), zirconium (Zr), hafnium (HI), terbium (Tb), thulium (Tm), cerium (Ce), dysprosium (Dy), erbium (Er), europium (Eu), holmium (Ho), iron (Fe), lanthanum (La), neodymium (Nd), praseodymium (Pr), lutetium (Lu) and any mixture thereof.

7. The method according to claim 4, wherein the inorganic material is selected from a hafnium oxide, rhenium oxide, europium oxide, a mixture of zirconium and of an inorganic oxide, and any mixture thereof.

8. The method according to claim 1, wherein the inorganic nanoparticles comprise a mixture of an inorganic oxide and of a metal.

9. The method according to claim 1, wherein the largest dimension of a nanoparticle is between about 5 nm and about 250 nm.

10. The method according to claim 1, said method comprising determining the electron density of the volume of the composition comprising the inorganic nanoparticles (Vc) and administering to the human subject a volume of the inorganic nanoparticles that occupies between 2.5% and 50% of the tumor volume.

11. The method according to claim 1, wherein the method comprises a step of calculating the quantity of electrons provided by the inorganic nanoparticles to the tumor using the following formula:

$$\text{Quantity of electrons} = V_{NP}(\text{cm}^3) \times \rho_{e^-\ material},$$

with $\rho_{e^-\ material} = d_{material} \times e^-_{material}$ and $V_{NP}$ (cm3) $= X_{mean} \times$ Vc (cm$^3$)/$d_{material}$ (g/cm$^3$)/1000 (cm$^3$), wherein $d_{material}$ is the theoretical (bulk) density of material constituting the inorganic nanoparticles, $e^-_{material}$ is the number of electrons per gram of the material constituting the inorganic nanoparticles, Vc represents volume composition and corresponds to the volume of the suspension of inorganic nanoparticles which is administered to the subject, and $X_{mean}$ corresponds to the concentration of the inorganic nanoparticle suspension which is injected into the tumor.

12. The method according to claim 11, wherein the inorganic nanoparticles comprise an inorganic material that has an effective atomic number ($Z_{eff}$) of at least 40.

* * * * *